US010066114B2

(12) United States Patent
Jackson et al.

(10) Patent No.: US 10,066,114 B2
(45) Date of Patent: Sep. 4, 2018

(54) INK JET DELIVERY SYSTEM COMPRISING AN IMPROVED PERFUME MIXTURE

(71) Applicant: The Procter & Gamble Company, Cincinnati, OH (US)

(72) Inventors: Rhonda Jean Jackson, Cincinnati, OH (US); Ronald David Turner, Walton, KY (US); Dana Paul Gruenbacher, Fairfield, OH (US); George Kavin Morgan, III, Hamilton, OH (US); Steven Louis Diersing, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/024,673

(22) Filed: Sep. 12, 2013

(65) Prior Publication Data

US 2014/0078229 A1 Mar. 20, 2014

Related U.S. Application Data

(60) Provisional application No. 61/700,937, filed on Sep. 14, 2012.

(51) Int. Cl.
*A61L 9/14* (2006.01)
*B41J 2/35* (2006.01)
*C09D 11/40* (2014.01)

(52) U.S. Cl.
CPC .............. *C09D 11/40* (2013.01); *A61L 9/14* (2013.01); *A61L 2209/135* (2013.01)

(58) Field of Classification Search
CPC ........... C11D 9/44; C11D 9/442; C11D 9/444; C11D 9/446; C11D 9/448; C11D 9/48; C11D 3/50; C11D 3/502; C11D 3/505; C11D 3/507; C11D 9/40; C11B 9/00; C11B 3/00; A61Q 13/00; B41J 2002/14346; B41J 2002/14427; B41J 2002/1648; B41J 2/32; B41J 2/335; B41J 2202/00; B41J 2202/01; B41J 2202/02; B41J 2/135; B41J 2/14; B41J 2/14008; B41J 2/14016; B41J 2/175; A61L 2202/15; A61L 9/14; A61L 2209/135; A61L 9/037; A61L 9/27; B01F 2215/0031; B01F 2215/0077; B01F 3/04021; B01D 1/16; B05B 1/00; B05B 1/005

See application file for complete search history.

(56) References Cited

U.S. PATENT DOCUMENTS

| 3,465,350 A | 9/1969 | Keur et al. |
| 3,465,351 A | 9/1969 | Keur et al. |
| 3,967,286 A * | 6/1976 | Andersson et al. ............ 347/87 |
| 4,532,530 A | 7/1985 | Hawkins |
| 5,084,713 A | 1/1992 | Wong |
| 5,317,339 A | 5/1994 | Braun |
| 5,591,409 A * | 1/1997 | Watkins ........................ 422/110 |
| 5,610,635 A | 3/1997 | Murray |
| 5,666,140 A | 9/1997 | Mitani et al. |
| 5,714,989 A | 2/1998 | Wade et al. |
| 5,874,974 A | 2/1999 | Courian et al. |
| 5,975,675 A | 11/1999 | Kim |
| 6,010,210 A | 1/2000 | Wilson et al. |
| 6,012,799 A | 1/2000 | Silverbrook |
| 6,024,440 A | 2/2000 | Murthy et al. |
| 6,113,228 A | 9/2000 | Pawlowski |
| 6,126,277 A | 10/2000 | Feinn et al. |
| 6,139,131 A | 10/2000 | Prasad et al. |
| 6,170,937 B1 | 1/2001 | Childers et al. |
| 6,261,347 B1 | 7/2001 | Moreland |
| 6,282,458 B1 | 8/2001 | Muray et al. |
| 6,287,550 B1 * | 9/2001 | Trinh ................... A01K 1/0152 119/171 |
| 6,322,200 B1 | 11/2001 | Feinn et al. |
| 6,325,475 B1 * | 12/2001 | Hayes ...................... A61B 5/00 128/203.11 |
| 6,371,451 B1 * | 4/2002 | Choi ...................... A45D 34/02 261/115 |
| 6,543,887 B2 | 4/2003 | Chang |
| 6,672,129 B1 | 1/2004 | Frederickson et al. |
| 6,698,862 B1 | 3/2004 | Chol |
| 6,808,684 B2 | 10/2004 | Boden et al. |
| 6,834,937 B2 | 12/2004 | Killmeier et al. |
| 7,097,263 B2 * | 8/2006 | Silverbrook ...................... 347/2 |
| 7,201,916 B2 | 4/2007 | Schiavo |
| 7,223,361 B2 | 5/2007 | Kvietok et al. |
| 7,293,849 B2 | 11/2007 | Tani et al. |
| 7,328,974 B2 | 2/2008 | Wang |
| 7,367,661 B2 | 5/2008 | Hess et al. |
| 7,389,943 B2 | 6/2008 | Jaworski |
| 7,490,815 B2 | 2/2009 | Tollens et al. |
| 7,499,632 B2 | 3/2009 | Granger |
| 7,669,978 B2 * | 3/2010 | Spivey ................. B41J 2/14072 347/47 |
| 8,020,573 B2 | 9/2011 | Lamers et al. |
| 8,087,759 B2 | 1/2012 | Oikawa et al. |
| 8,101,124 B2 | 1/2012 | Uchiyama |
| 8,142,558 B2 | 3/2012 | Robertson et al. |

(Continued)

FOREIGN PATENT DOCUMENTS

| CA | 2 213 066 A1 | 2/1999 |
| CA | 2213066 | 2/1999 |

(Continued)

OTHER PUBLICATIONS

PCT Search report dated Nov. 18, 2013; 9 Pages; PCT/US2013/059576.

(Continued)

*Primary Examiner* — Patrick King
(74) *Attorney, Agent, or Firm* — Abby A. Lopez

(57) ABSTRACT

Ink jet delivery systems comprising a fluid composition comprising a perfume mixture having a boiling point of less than 250° C. and an ink jet to deliver the fluid composition into the air, whereby scent longevity, perfume character, room fill, and/or functional benefits (e.g. odor elimination) are provided.

14 Claims, No Drawings

(56) References Cited

U.S. PATENT DOCUMENTS

| | | | |
|---|---|---|---|
| 8,201,752 B2* | 6/2012 | Brodbeck | A01M 1/2077 239/13 |
| 8,251,500 B2 | 8/2012 | Yamanda et al. | |
| 8,727,234 B2 | 5/2014 | Haran | |
| 8,821,802 B2* | 9/2014 | Haran | A61L 9/122 422/120 |
| 8,870,090 B2 | 10/2014 | Feriani | |
| 8,881,999 B2 | 11/2014 | Blaylock et al. | |
| 9,174,453 B1 | 11/2015 | Dodd et al. | |
| 9,211,356 B2 | 12/2015 | Gruenbacher et al. | |
| 9,211,980 B1 | 12/2015 | Gruenbacher | |
| 9,377,786 B2 | 6/2016 | Nakamoto et al. | |
| 9,554,459 B2 | 1/2017 | Gruenbacher et al. | |
| 9,636,430 B2 | 5/2017 | Gruenbacher et al. | |
| 2001/0050317 A1 | 12/2001 | Denen | |
| 2002/0050533 A1 | 5/2002 | Hirota | |
| 2002/0063752 A1 | 5/2002 | Clark | |
| 2002/0086319 A1* | 7/2002 | Ellson et al. | 435/6 |
| 2002/0192255 A1 | 12/2002 | Schiavo | |
| 2003/0062385 A1* | 4/2003 | Engel | A45D 34/04 222/137 |
| 2003/0218077 A1 | 11/2003 | Boticki | |
| 2004/0032468 A1 | 2/2004 | Killmeier et al. | |
| 2004/0119793 A1* | 6/2004 | Mutz et al. | 347/75 |
| 2004/0200907 A1 | 10/2004 | Martens et al. | |
| 2005/0018016 A1 | 1/2005 | Silverbrook | |
| 2005/0037945 A1 | 2/2005 | Gygax et al. | |
| 2005/0062804 A1 | 3/2005 | Eaton | |
| 2005/0077376 A1 | 4/2005 | Hess et al. | |
| 2005/0091879 A1* | 5/2005 | DuVal et al. | 34/597 |
| 2005/0124512 A1 | 6/2005 | Woo et al. | |
| 2005/0205916 A1 | 9/2005 | Conway et al. | |
| 2005/0279854 A1 | 12/2005 | Martens et al. | |
| 2006/0065755 A1 | 3/2006 | Sugita et al. | |
| 2006/0152550 A1 | 7/2006 | Tomita | |
| 2007/0008380 A1 | 1/2007 | Ushinohama | |
| 2007/0010645 A1 | 1/2007 | Vonwiller et al. | |
| 2007/0207174 A1* | 9/2007 | Pluyter | A61K 8/11 424/401 |
| 2007/0222830 A1* | 9/2007 | Moynihan | A21C 14/00 347/85 |
| 2008/0023569 A1 | 1/2008 | O'Leary et al. | |
| 2008/0043063 A1 | 2/2008 | Bergstedt | |
| 2008/0061163 A1* | 3/2008 | Kubby et al. | 239/102.1 |
| 2008/0073443 A1* | 3/2008 | Tollens | A01M 1/2044 239/4 |
| 2008/0197213 A1 | 8/2008 | Flashinski et al. | |
| 2009/0096839 A1 | 4/2009 | Olbrich et al. | |
| 2009/0108094 A1* | 4/2009 | Ivri | A61L 9/14 239/101 |
| 2009/0126722 A1 | 5/2009 | Sugita et al. | |
| 2009/0289127 A1* | 11/2009 | Tollens | A01M 1/205 239/4 |
| 2010/0001091 A1 | 1/2010 | Bara et al. | |
| 2010/0154790 A1 | 6/2010 | Merassi et al. | |
| 2010/0206306 A1* | 8/2010 | Feriani et al. | 128/203.12 |
| 2010/0328957 A1 | 12/2010 | Hessing | |
| 2011/0024521 A1 | 2/2011 | Joergensen | |
| 2011/0036365 A1 | 2/2011 | Chong et al. | |
| 2011/0049266 A1 | 3/2011 | Joergensen | |
| 2011/0089252 A1 | 4/2011 | Rosener et al. | |
| 2011/0130877 A1* | 6/2011 | Lynch | 700/258 |
| 2011/0221083 A1 | 9/2011 | Laulicht | |
| 2011/0284653 A1* | 11/2011 | Butler et al. | 239/34 |
| 2011/0284656 A1* | 11/2011 | Kambayashi et al. | 239/102.2 |
| 2011/0290911 A1 | 12/2011 | Tollens et al. | |
| 2012/0093491 A1* | 4/2012 | Browder | A61L 9/015 392/390 |
| 2012/0097754 A1* | 4/2012 | Vlad et al. | 239/6 |
| 2013/0010035 A1 | 1/2013 | Norikane | |
| 2013/0026250 A1* | 1/2013 | Burt | A01M 1/205 239/302 |
| 2013/0206857 A1 | 8/2013 | Ivri | |
| 2013/0292484 A1 | 11/2013 | Jackson | |
| 2014/0078229 A1 | 3/2014 | Jackson et al. | |
| 2014/0369895 A1* | 12/2014 | Turner et al. | 422/124 |
| 2015/0367013 A1 | 12/2015 | Gruenbacher et al. | |
| 2015/0367014 A1 | 12/2015 | Gruenbacher et al. | |
| 2015/0367016 A1 | 12/2015 | Gruenbacher et al. | |
| 2015/0367356 A1 | 12/2015 | Gruenbacher et al. | |
| 2015/0368001 A1 | 12/2015 | Gruenbacher et al. | |
| 2016/0271639 A1 | 9/2016 | Bush et al. | |
| 2016/0354799 A1 | 12/2016 | Gruenbacher et al. | |
| 2017/0072085 A1 | 3/2017 | Gruenbacher et al. | |
| 2017/0072086 A1 | 3/2017 | Gruenbacher et al. | |
| 2017/0094720 A1 | 3/2017 | Gruenbacher et al. | |
| 2017/0165390 A1 | 6/2017 | Gruenbacher et al. | |

FOREIGN PATENT DOCUMENTS

| | | | | |
|---|---|---|---|---|
| CN | 1393491 A | * | 1/2003 | |
| CN | 1223637 C | | 10/2005 | |
| CN | 101 020 073 A | | 8/2007 | |
| CN | 101020073 A | * | 8/2007 | |
| CN | 204072869 U | | 1/2015 | |
| EP | 1510228 A1 | | 3/2005 | |
| EP | 1894727 A2 | | 3/2008 | |
| EP | 2143576 B1 | | 11/2012 | |
| GB | 2410468 A | | 3/2005 | |
| JP | H09123453 A | | 5/1997 | |
| JP | 2002254613 A | | 9/2002 | |
| JP | A-2004-311093 | | 11/2004 | |
| JP | 2005185366 A | | 7/2005 | |
| JP | 2005224503 A | | 8/2005 | |
| JP | 2005224504 A | | 8/2005 | |
| JP | A2005224504 | | 8/2005 | |
| JP | 2007054446 A | | 3/2007 | |
| JP | A-2008-061937 | | 3/2008 | |
| JP | A-2009-213901 | | 9/2009 | |
| KR | 100238582 B1 | | 1/2000 | |
| WO | WO 01/30404 A1 | | 5/2001 | |
| WO | WO 2004/044552 A2 | | 5/2004 | |
| WO | WO 2006/004902 A1 | | 1/2006 | |
| WO | WO 2007/083164 A2 | | 7/2007 | |
| WO | WO 2014/043424 A1 | | 3/2014 | |
| WO | WO 2015/175527 A2 | | 11/2015 | |
| WO | WO 2015195994 A1 | * | 12/2015 | B05B 1/24 |

OTHER PUBLICATIONS

"Perfume and Flavor Chemicals (Aroma Chemicals)," written and published by Steffen Arctander, 1969.

* cited by examiner

INK JET DELIVERY SYSTEM COMPRISING AN IMPROVED PERFUME MIXTURE

FIELD OF THE INVENTION

The present invention relates to an ink jet delivery system comprising an improved perfume mixture and a method of delivering a perfume mixture into the air.

BACKGROUND OF THE INVENTION

Various systems exist to deliver volatile compositions, such as perfume mixtures, into the air by an energized (i.e. electrically/battery powered) atomization system. Such attempts include battery-powered automatic aerosol air fresheners, sold under the tradename AIRWICK by Reckitt Benckiser. Another attempt is a piezoelectric actuator that atomizes a volatile composition into fluid droplets in the air, sold under the tradename GLADE by S.C. Johnson & Son.

Recent attempts have been made to deliver scents by means of an ink jet head. But, these attempts are directed to printing ink-based scented fluids onto a substrate or surface medium. As such, there remains a need to effectively deliver a perfume mixture into the air via an ink jet delivery system.

SUMMARY OF THE INVENTION

In one embodiment, there is provided a delivery system comprising a fluid composition comprising from about 50% to about 100%, by weight of said composition, of a perfume mixture, wherein about 3% to about 25%, by weight of said perfume mixture, has a boiling point less than 250° C.; and an ink jet head for delivering said fluid composition into the air.

In another embodiment, there is provided a delivery system comprising a fluid composition comprising from about 50% to about 100%, by weight of said composition, of a perfume mixture, wherein about 3% to about 25%, by weight of said perfume mixture, has a boiling point less than 200° C.; a reservoir containing said fluid composition and at least partially containing a wick; and an ink jet head in fluid communication with said wick and comprising and 8 to 32 nozzles, wherein said ink jet head emits 1-4 picoliters of said fluid composition into the air from each of said 8 to 32 nozzles.

DETAILED DESCRIPTION OF EMBODIMENTS

The present invention provides a delivery system comprising an ink jet and a volatile composition and methods for delivering such volatile compositions into the air by an ink jet.

Delivery system may comprise a reservoir containing a fluid composition, an ink jet head, a power source, and a housing for containing such elements. It is to be understood that the delivery system is not limited to the construction and arrangement of the components set forth in the following description or illustrated in the drawings. The invention is applicable to other embodiments or of being practiced or carried out in various ways.

Ink Jet Head

The delivery system of the present invention employs an ink jet head typically used in ink jet printing. There are two major categories of ink jet printing: "drop-on-demand" and "continuous" ink jet printing.

For continuous ink jet printing, an ink is supplied under pressure to an ink jet nozzle and forced out through a small orifice. Prior to passing out of the nozzle, the pressurized ink stream proceeds through a ceramic crystal which is subjected to an electric current. This current causes a piezoelectric vibration equal to the frequency of the AC electric current. This vibration, in turn, generates the ink droplets from the unbroken ink stream. The ink stream breaks up into a continuous series of drops which are equally spaced and of equal size. Surrounding the jet, at a point where the drops separate from the fluid stream in a charge electrode, a voltage is applied between the charge electrode and the drop stream. When the drops break off from the stream, each drop carries a charge proportional to the applied voltage at the instant at which it breaks off. By varying the charge electrode voltages at the same rate as drops are produced, it is possible to charge every drop to a predetermined level. The drop stream continues its flight and passes between two deflector plates which are maintained at a constant potential. In the presence of this field, a drop is deflected towards one of the plates by an amount proportional to the charge carried. Drops which are uncharged are undeflected and collected into a gutter to be recycled to the ink nozzle. Those drops which are charged, and hence deflected, impinge on a substrate traveling at a high speed at right angles to the direction of drop deflection. By varying the charge on individual drops, the desired pattern can be printed.

In a typical "drop-on-demand" ink jet printing process, a fluid ink is forced under pressure through a very small orifice of a diameter typically about 0.0024 inches (5-50 microns) in the form of minute droplets by rapid pressure impulses. The rapid pressure impulses are typically generated in the print head by either expansion of a piezoelectric crystal vibrating at a high frequency or volatilization of a volatile composition (e.g. solvent, water, propellant) within the ink by rapid heating cycles. The piezoelectric crystal expansion causes the ink to pass through the orifice as minute droplets in proportion to the number of crystal vibrations. Thermal ink jet printers employ a heating element within the print head to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may be energized to achieve an electrical charge and deflected as in the continuous ink jet printing. Conventional ink jet printers are more particularly described in U.S. Pat. Nos. 3,465,350 and 3,465,351.

Another type of ink jet printing process is an electrostatic ink jet process which employs an electrostatic field to draw the ink through the nozzle to the substrate. Charged ink droplets are drawn to an oppositely charged platen behind the receiving substrate. Such devices have been developed by Technology International Corp. of Boulder, Colo., under the trade name ESIJET.

While the present invention may employ any of the above described ink jet head delivery processes, the ink jet head of the present invention may include a membrane of 8 to 48 nozzles, alternatively 8 to 32 nozzles, alternatively 8 to 16 nozzles, alternatively 8 to 12 nozzles, that delivers 1-4 picoliters of fluid composition per nozzle, alternatively 1-2 picoliters per nozzle on an ink jet head that may be less than about 25 $mm^2$. In some embodiments, the ink jet head delivers from about 5 mg to about 40 mg of fluid composition per hour into the air. One type of membrane suitable for the present invention is an integrated membrane of nozzles obtained via MEMs technology as described in US 2010/0154790.

Reservoir

The delivery system includes a reservoir for containing the fluid composition. In some embodiments, the reservoir is configured to contain from about 5 to about 50 ml of fluid composition, alternatively from about 10 to about 30 ml of fluid composition, alternatively from about 15 to about 20 ml of fluid composition. The delivery system may be configured to have multiple reservoirs, each containing the same or a different composition. The reservoir may be formed as a separate construction, so as to be replaceable (e.g. a refill). The reservoir can be made of any suitable material for containing a fluid composition. Suitable materials for the containers include, but are not limited to, glass and plastic. Examples of such reservoirs are readily available in the marketplace.

The reservoir may comprise a capillary element made of any commercially available wicking material such as a fibrous or porous wick that contains multiple interconnected open cells which form capillary passages to draw a fluid composition up from the reservoir to come in contact with the fluid feed of the ink jet engine. Non-limiting examples of suitable compositions for the capillary element include polyethylene, ultra-high molecular weight polyethelene (UHMW), nylon 6 (N6), polypropylene (PP), polyester fibers, ethyl vinyl acetate, polyether sulfone, polyvinylidene fluoride (PVDF), and polyethersulfone (PES), polytetrafluoroethylene (PTFE), and combinations thereof.

In some embodiments, the capillary element may be a high density wick composition to aid in containing the scent of a perfume mixture. In one embodiment, the capillary element is made from a plastic material chosen from high-density polyethylene (HDPE). As used herein, high density wick compositions include any conventional wick material known in the art having a pore diameter or equivalent pore diameter (e.g. in the case of fiber based wicks) ranging from about 20 microns to about 150 microns, alternatively from about 30 microns to about 70 microns, alternatively from about 30 microns to about 50 microns, alternatively, about 40 microns to about 50 microns.

In some embodiments, the capillary element is free of a polyurethane foam. Many ink jet cartridges use an open cell polyurethane foam which can be incompatible with perfume mixtures over time (e.g. after 2 or 3 months) and can break down.

Regardless of the material of manufacture, the capillary element can exhibit an average pore size from about 10 microns to about 500 microns, alternatively from about 50 microns to about 150 microns, alternatively about 70 microns. The average pore volume of the wick is from about 15% to about 85%, alternatively from about 25% to about 50%. Good results have been obtained with wicks having an average pore volume of about 38%. The capillary element can also be of variable length, such as, from about 1 mm to about 100 mm, or from about 5 mm to about 75 mm, or from about 10 mm to about 50 mm.

The capillary element is in fluid communication with the fluid composition and may extend at least partially outside the reservoir. In some embodiments, the capillary element may be completely surrounded by the walls of the reservoir. Depending upon the configuration of the delivery system, a fluid composition may travel up or down the capillary element. After flowing from the reservoir, the fluid composition may continue traveling downstream to a holding tank from which the ink jet head draws fluid from to atomize the fluid into the air.

In some embodiments, the delivery system may include a fluid channel positioned in a flow path between the capillary element and the holding tank. A channel may be useful in configurations where the reservoir and holding tank are placed laterally from one another. The length of the channel, measured from the capillary element to center of the reservoir, may be about 12 mm, alternatively about 13 mm, alternatively, about 14 mm, alternatively about 15 mm, alternatively about 11 mm, alternatively about 10 mm.

Fluid Composition

To operate satisfactorily within an ink jet delivery system, many characteristics of a fluid composition are taken into consideration. Some factors include formulating fluids with viscosities that are optimal to emit from the ink jet head, formulating fluids with limited amounts or no suspended solids that would clog the ink jet head, formulating fluids to be sufficiently stable to not dry and clog the ink jet head, etc. Operating satisfactorily within an ink jet delivery system, however, addresses only some of the requirements necessary for a fluid composition having more than 50 wt % of a perfume mixture to atomize properly from an ink jet delivery system and to be delivered effectively as an air freshening or malodor reducing composition.

The fluid composition of the present invention may exhibit a viscosity of less than 20 centipoise ("cps"), alternatively less than 18 cps, alternatively less than 16 cps, alternatively from about 5 cps to about 16 cps, alternatively about 8 cps to about 15 cps. And, the volatile composition may have surface tensions below about 35, alternatively from about 20 to about 30 dynes per centimeter. Viscosity is in cps, as determined using the Bohlin CVO Rheometer system in conjunction with a high sensitivity double gap geometry.

In some embodiments, the fluid composition is free of suspended solids or solid particles existing in a mixture wherein particulate matter is dispersed within a liquid matrix. Free of suspended solids is distinguishable from dissolved solids that are characteristic of some perfume materials.

The fluid composition of the present invention comprises a perfume mixture present in an amount greater than about 50%, by weight of the fluid composition, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%. In some embodiments, the fluid composition may consist entirely of the perfume mixture (i.e. 100 wt. %).

The perfume mixture may contain one or more perfume materials. The perfume materials are selected based on the material's boiling point ("B.P."). The B.P. referred to herein is measured under normal standard pressure of 760 mm Hg. The B.P. of many perfume ingredients, at standard 760 mm Hg can be found in "Perfume and Flavor Chemicals (Aroma Chemicals)," written and published by Steffen Arctander, 1969.

In the present invention, the perfume mixture may have a B.P. of less than 250° C., alternatively less than 225° C., alternatively less than 200° C., alternatively less than about 150° C., alternatively less than about 120° C., alternatively less than about 100° C., alternatively about 50° C. to about 200° C., alternatively about 110° C. to about 140° C. In some embodiments, about 3 wt % to about 25 wt % of the perfume mixture has a B.P. of less than 200° C., alternatively about 5 wt % to about 25 wt % of the perfume mixture has a B.P. of less than 200° C.

Table 1 lists some non-limiting, exemplary individual perfume materials suitable for the perfume mixture of the present invention.

TABLE 1

| CAS Number | Perfume Raw Material Name | B.P. (° C.) |
|---|---|---|
| 105-37-3 | Ethyl propionate | 99 |
| 110-19-0 | Isobutyl acetate | 116 |
| 928-96-1 | Beta gamma hexenol | 157 |
| 80-56-8 | Alpha Pinene | 157 |
| 127-91-3 | Beta Pinene | 166 |
| 1708-82-3 | cis-hexenyl acetate | 169 |
| 124-13-0 | Octanal | 170 |
| 470-82-6 | Eucalyptol | 175 |
| 141-78-6 | Ethyl acetate | 77 |

Table 2 shows an exemplary perfume mixture having a total B.P. less than 200° C.

TABLE 2

| CAS Number | Perfume Raw Material Name | Wt % | B.P. (° C.) |
|---|---|---|---|
| 123-68-2 | Allyl Caproate | 2.50 | 185 |
| 140-11-4 | Benzyl Acetate | 3.00 | 214 |
| 928-96-1 | Beta Gamma Hexenol | 9.00 | 157 |
| 18479-58-8 | Dihydro Myrcenol | 5.00 | 198 |
| 39255-32-8 | Ethyl 2 Methyl Pentanoate | 9.00 | 157 |
| 77-83-8 | Ethyl Methyl Phenyl Glycidate | 2.00 | 260 |
| 7452-79-1 | Ethyl-2-Methyl Butyrate | 8.00 | 132 |
| 142-92-7 | Hexyl Acetate | 12.50 | 146 |
| 68514-75-0 | Orange Phase Oil 25X1.18%-Low Cit. 14638 | 10.00 | 177 |
| 93-58-3 | Methyl Benzoate | 0.50 | 200 |
| 104-93-8 | Para Cresyl Methyl Ether | 0.20 | 176 |
| 1191-16-8 | Prenyl Acetate | 8.00 | 145 |
| 88-41-5 | Verdox | 3.00 | 223 |
| 58430-94-7 | Iso Nonyl Acetate | 27.30 | 225 |
| | TOTAL: | 100.00 | |

When formulating fluid compositions for the present invention, one may also include solvents, diluents, extenders, fixatives, thickeners, or the like. Non-limiting examples of these materials are ethyl alcohol, carbitol, diethylene glycol, dipropylene glycol, diethyl phthalate, triethyl citrate, isopropyl myristate, ethyl cellulose, and benzyl benzoate.

In some embodiments, the fluid composition may contain functional perfume components ("FPCs"). FPCs are a class of perfume raw materials with evaporation properties that are similar to traditional organic solvents or volatile organic compounds ("VOCs"). "VOCs", as used herein, means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether. VOCs are commonly used at levels greater than 20% in a fluid composition to aid in perfume evaporation.

The FPCs of the present invention aid in the evaporation of perfume materials and may provide a hedonic, fragrance benefit. FPCs may be used in relatively large concentrations without negatively impacting perfume character of the overall composition. As such, in some embodiments, the fluid composition of the present invention may be substantially free of VOCs, meaning it has no more than 18%, alternatively no more than 6%, alternatively no more than 5%, alternatively no more than 1%, alternatively no more than 0.5%, by weight of the composition, of VOCs. The volatile composition, in some embodiments, may be free of VOCs.

Perfume materials that are suitable as a FPC may have a KI, as defined above, from about 800 to about 1500, alternatively about 900 to about 1200, alternatively about 1000 to about 1100, alternatively about 1000.

Perfume materials that are suitable for use as a FPC can also be defined using odor detection threshold ("ODT") and non-polarizing scent character for a given perfume character scent camp. ODTs may be determined using a commercial GC equipped with flame ionization and a sniff-port. The GC is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be calculated. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability. The necessary amount of analyte is injected onto the column to achieve a 50 ppb concentration at the detector. Typical GC parameters for determining ODTs are listed below. The test is conducted according to the guidelines associated with the equipment.

Equipment:
GC: 5890 Series with FID detector (Agilent Technologies, Ind., Palo Alto, Calif., USA);
7673 Autosampler (Agilent Technologies, Ind., Palo Alto, Calif., USA);
Column: DB-1 (Agilent Technologies, Ind., Palo Alto, Calif., USA) Length 30 meters ID 0.25 mm film thickness 1 micron (a polymer layer on the inner wall of the capillary tubing, which provide selective partitioning for separations to occur).

Method Parameters:
Split Injection: 17/1 split ratio;
Autosampler: 1.13 microliters per injection;
Column Flow: 1.10 mL/minute;
Air Flow: 345 mL/minute;
Inlet Temp. 245° C.;
Detector Temp. 285° C.

Temperature Information:
Initial Temperature: 50° C.;
Rate: 5C/minute;
Final Temperature: 280° C.;
Final Time: 6 minutes;
Leading assumptions: (i) 12 seconds per sniff
(ii) GC air adds to sample dilution.

FPCs may have an ODT from greater than about 1.0 parts per billion ("ppb"), alternatively greater than about 5.0 ppb, alternatively greater than about 10.0 ppb, alternatively greater than about 20.0 ppb, alternatively greater than about 30.0 ppb, alternatively greater than about 0.1 parts per million.

In one embodiment, the FPCs in a fluid composition of the present invention may have a KI in the range from about 900 to about 1400; alternatively from about 1000 to about 1300.

These FPCs can be either an ether, an alcohol, an aldehyde, an acetate, a ketone, or mixtures thereof.

FPCs may be highly volatile, low B.P. perfume materials. Exemplary FPC include iso-nonyl acetate, dihydro myrcenol (3-methylene-7-methyl octan-7-ol), linalool (3-hydroxy-3, 7-dimethyl-1,6 octadiene), geraniol (3,7 dimethyl-2,6-octadien-1-ol), d-limonene (1-methyl-4-isopropenyl-1-cyclohexene, benzyl acetate, isopropyl mystristate, and mixtures thereof. Table 3 lists the approximate reported values for exemplary properties of certain FPCs.

TABLE 3

| FPC | B.P. (° C.) | MW | Clog P @ 25° C. | Flash point (° C.) | Vapor pressure | KI | ODT |
|---|---|---|---|---|---|---|---|
| Iso-Nonyl Acetate (CAS# 58430-94-7) | 225 | 186.3 | 4.28 | 79.4 | 0.11 | 1178 | 12 ppb |
| Dihydro Myrcenol (CAS# 18479-58-8) | 198 | 156.3 | 3.03 | 76.1 | 0.1 | 1071 | 32 ppb |
| Linalool (CAS# 78-70-6) | 205 | 154.3 | 2.549 | 78.9 | 0.05 | 1107 | 22 ppb |
| Geraniol (CAS# 106-24-1) | 237 | 154.3 | 2.769 | 100 | 0.00519 | 1253 | 0.4 ppb |
| D-Limonene (CAS# 94266-47-4) | 170 | 136 | 4.35 | 47.2 | 1.86 | 1034 | 204 ppb |

The total amount of FPCs in the perfume mixture may be greater than about 50%, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 75% to about 100%, alternatively from about 80% to about 100%, alternatively from about 85% to about 100%, alternatively from about 90% to about 100%, alternatively about 100%, by weight of the perfume mixture. In some embodiments, the perfume mixture may consist entirely of FPCs (i.e. 100 wt. %).

For purposes of illustrating the present invention in further detail, Table 4 lists a non-limiting, exemplary fluid composition comprising FPCs and their approximate reported values for KI and B.P.

TABLE 4

| Material Name | KI | wt. % | B.P. (° C.) |
|---|---|---|---|
| Benzyl Acetate (CAS # 140-11-4) | 1173 | 1.5 | 214 |
| Ethyl-2-methyl Butyrate (CAS # 7452-79-1) | 850 | 0.3 | 132 |
| Amyl Acetate (CAS # 628-63-7) | 912 | 1.0 | 149 |
| Cis 3 Hexenyl Acetate (CAS # 3681-71-8) | 1009 | 0.5 | 169 |
| Ligustral (CAS # 27939-60-2) | 1094 | 0.5 | 177 |
| Melonal (CAS # 106-72-9) | 1060 | 0.5 | 116 |
| Hexyl Acetate (CAS # 142-92-7) | 1016 | 2.5 | 146 |
| Dihydro Myrcenol (CAS# 18479-58-8) | 1071 | 15 | 198 |
| Phenyl Ethyl Alcohol (CAS# 60-12-8) | 1122 | 8 | 219 |
| Linalool (CAS # 78-70-6) | 1243 | 25.2 | 205 |
| Geraniol (CAS# 106-24-1) | 1253 | 5 | 238 |
| Iso Nonyl Acetate (CAS # 40379-24-6) | 1295 | 22.5 | 225 |
| Benzyl Salicylate (CAS # 118-58-1) | 2139 | 3 | 320 |
| Coumarin (CAS # 91-64-5) | 1463 | 1.5 | 267 |
| Methyl Dihydro Jasmonate (CAS# 24851-98-7) | 1668 | 7 | 314 |
| Hexyl Cinnamic Aldehyde (CAS # 101-86-0) | 1770 | 6 | 305 |

It is contemplated that the fluid composition may comprise other volatile materials in addition to or in substitution for the perfume mixture including, but not limited to, volatile dyes; compositions that function as insecticides; essential oils or materials that acts to condition, modify, or otherwise modify the environment (e.g. to assist with sleep, wake, respiratory health, and like conditions); deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

Optional Features

Fan

In another aspect of the invention, the delivery system may comprise a fan to assist in driving room-fill and to help avoid deposition of larger droplets from landing on surrounding surfaces that could damage the surface. The fan may be any known fan used in the art for air freshening systems that delivers 1-1000 cubic centimeters of air/minute, alternatively 10-100 cubic centimeters/minute.

Sensors

In some embodiments, the delivery system may include commercially available sensors that respond to environmental stimuli such as light, noise, motion, and/or odor levels in the air. For example, the delivery system can be programmed to turn on when it senses light, and/or to turn off when it senses no light. In another example, the delivery system can turn on when the sensor senses a person moving into the vicinity of the sensor. Sensors may also be used to monitor the odor levels in the air. The odor sensor can be used to turn-on the delivery system, increase the heat or fan speed, and/or step-up the delivery of the fluid composition from the delivery system when it is needed.

The sensor may also be used to measure fluid levels in the reservoir to indicate the reservoir's end-of-life in advance of depletion. In such case, an LED light may turn on to indicate the reservoir needs to be filled or replaced with a new reservoir.

The sensors may be integral with the delivery system housing or in a remote location (i.e. physically separated from the delivery system housing) such as remote computer or mobile smart device/phone. The sensors may communicate with the delivery system remotely via low energy blue tooth, 6 low pan radios or any other means of wirelessly communicating with a device and/or a controller (e.g. smart phone or computer).

Portable/Battery

The delivery system may be configured to be compact and easily portable. In such case, the delivery system may be battery operated. The delivery system may be capable for use with electrical sources as 9-volt batteries, conventional dry cells such as "A", "AA", "AAA", "C", and "D" cells, button cells, watch batteries, solar cells, as well as rechargeable batteries with recharging base.

Programming

The delivery system may include programmable electronics to set a precise intensity level and delivery rate (in milligrams per hour). Alternatively, the electronic circuitry of the delivery system may allow a user to adjust the intensity and/or the timing of the delivering the fluid composition for personal preference, efficacy, or for room size. For example, the delivery system may provide 5 intensity levels for a user to select and user selected options of delivering the fluid composition every 6, 12, or 24 hours.

In multiple reservoir delivery systems, a microprocessor and timer could be installed to emit the fluid composition from individual reservoirs at different times and for selected time periods, including emitting the volatile compositions in an alternating emission pattern as described in U.S. Pat. No. 7,223,361. Additionally, the delivery system could be programmable so a user can select certain compositions for emission. In the case of scented perfumes being emitted simultaneously, a customized scent may be delivered to the air.

Throughout this specification, components referred to in the singular are to be understood as referring to both a single or plural of such component.

All percentages stated herein are by weight unless otherwise specified.

Every numerical range given throughout this specification will include every narrower numerical range that falls within such broader numerical range, as if such narrower numerical range were all expressly written herein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

Further, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A delivery system comprising:
   a fluid composition comprising from 60% to 100%, by weight of said fluid composition, of a perfume mixture, wherein the perfume mixture consists of one or more perfume materials, wherein said perfume mixture has an weighted average boiling point of less than 250° C., wherein the fluid composition comprises a functional perfume component and wherein a balance of the fluid composition consists of materials selected from the group consisting of: solvents, diluents, extenders, fixatives, thickeners, and combinations thereof;
   a reservoir containing said fluid composition and at least partially containing a capillary element; and
   a thermal ink jet head in fluid communication with said capillary element, wherein the thermal ink jet head comprises a heating element and a nozzle, wherein the heating element is configured to volatilize a portion of the fluid composition to propel the fluid composition through the nozzle in the form of droplets that are emitted into the air, wherein the nozzle comprises an orifice having a diameter of 5 to 50 microns.

2. The delivery system of claim 1, wherein said composition comprises from about 70% to about 100%, by weight of said composition, of the perfume mixture.

3. The delivery system of claim 1, wherein said composition comprises from about 80% to about 100%, by weight of said composition, of the perfume mixture.

4. The delivery system of claim 1, wherein said composition comprises from about 90% to about 100%, by weight of said composition, of the perfume mixture.

5. The delivery system of claim 1, wherein about 3% to about 25% of the perfume mixture has an average boiling point less than 200° C.

6. The delivery system of claim 1, wherein said average boiling point of the perfume mixture is less than 200° C.

7. The delivery system of claim 1, wherein said average boiling point of the perfume mixture is less than 150° C.

8. The delivery system of claim 1, wherein said fluid composition is free of suspended solids.

9. The delivery system of claim 1 wherein said ink jet head comprises 8 to 48 nozzles and emits 1 to 4 picoliters of said fluid composition into the air.

10. The delivery system of claim 1, wherein said ink jet head comprises 16 to 32 nozzles and emits from about 5 mg to about 40 mg of said fluid composition per hour into the air.

11. The delivery system of claim 1 further comprising a sensor selected from the group consisting of a motion sensor, a light sensor, a fluid detection sensor, an odor detection sensor, and combinations thereof.

12. The delivery system of claim 1, wherein the functional perfume component is selected from the group consisting of: ethers, alcohols, aldehydes, acetates, ketones, or mixtures thereof.

13. The delivery system of claim 1, wherein the functional perfume component is selected from the group consisting of: aldehydes, acetates, ketones, or mixtures thereof.

14. The delivery system of claim 1, wherein the function perfume component has an odor detection threshold from greater than about 1.0 parts per billion.

* * * * *